(12) United States Patent
Lake et al.

(10) Patent No.: US 8,563,590 B2
(45) Date of Patent: *Oct. 22, 2013

(54) COMPOUNDS, COMPOSITIONS AND METHODS FOR THE TREATMENT OF ISLET AMYLOID POLYPEPTIDE (IAPP) ACCUMULATION IN DIABETES

(75) Inventors: Thomas Lake, Snohomish, WA (US); Alan D. Snow, Lynnwood, WA (US)

(73) Assignee: ProteoTech, Inc., Kirkland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/348,945

(22) Filed: Jan. 12, 2012

(65) Prior Publication Data

US 2013/0012555 A1    Jan. 10, 2013

Related U.S. Application Data

(62) Division of application No. 12/398,420, filed on Mar. 5, 2009, now abandoned.

(60) Provisional application No. 61/034,046, filed on Mar. 5, 2008.

(51) Int. Cl.
*A61K 31/415* (2006.01)

(52) U.S. Cl.
USPC .......................................... 514/396; 514/741

(58) Field of Classification Search
USPC .................................. 514/183, 741, 764, 396
See application file for complete search history.

(56) References Cited

U.S. PATENT DOCUMENTS

| 6,255,327 B1 | 7/2001 | Brenner et al. |
| 6,465,504 B1 | 10/2002 | Lattmann et al. |
| 6,596,750 B2 | 7/2003 | Lattmann et al. |
| 6,723,742 B2 | 4/2004 | Lattmann et al. |
| 2004/0127555 A1* | 7/2004 | Snow et al. ............. 514/464 |
| 2005/0235428 A1 | 10/2005 | Bachmann et al. |
| 2007/0225362 A1* | 9/2007 | Snow et al. ............. 514/464 |
| 2008/0187510 A1 | 8/2008 | Camenisch et al. |
| 2008/0279962 A1 | 11/2008 | Nick et al. |

FOREIGN PATENT DOCUMENTS

| WO | WO2006/120133 A2 | 11/2006 |
| WO | WO 2008/015021 * | 2/2008 |
| WO | WO2008/015021 A1 | 2/2008 |
| WO | WO2008/138912 A1 | 11/2008 |
| WO | WO2008/142094 A1 | 11/2008 |
| WO | 2009/111611 A2 | 9/2009 |
| WO | 2010/000372 A2 | 1/2010 |

* cited by examiner

*Primary Examiner* — Sreeni Padmanabhan
*Assistant Examiner* — Shobha Kantamneni
(74) *Attorney, Agent, or Firm* — Rebecca Eagen

(57) ABSTRACT

Dihydroxyaryl compounds and pharmaceutically acceptable esters, their synthesis, pharmaceutical compositions containing them, and their use in the treatment of IAPP or amylin fibril diseases, and the manufacture of medicaments for such treatment.

2 Claims, No Drawings

COMPOUNDS, COMPOSITIONS AND METHODS FOR THE TREATMENT OF ISLET AMYLOID POLYPEPTIDE (IAPP) ACCUMULATION IN DIABETES

CROSS-REFERENCE TO RELATED APPLICATIONS

This application is a divisional of U.S. patent application Ser. No. 12/398,420, filed on Mar. 5, 2009, which claimed priority to U.S. provisional application 61/034,046 filed on Mar. 5, 2008.

TECHNICAL FIELD

This invention relates to bis-dihydroxyaryl compounds and pharmaceutically acceptable salts, their synthesis, pharmaceutical compositions containing them, and their use in the treatment of islet amyloid polypeptide (IAPP) amyloid disease, such as observed in type 2 diabetes, and in the manufacture of medicaments for such treatment.

BACKGROUND OF THE INVENTION

A variety of human diseases demonstrate amyloid deposition and often involve systemic organs (i.e. organs or tissues lying outside the central nervous system), with the amyloid accumulation leading to organ dysfunction or failure. In these amyloid diseases, a single organ may be affected such as the pancreas in 90% of patients with type 2 diabetes. In this type of amyloid disease, the beta-cells in the islets of Langerhans in pancreas are believed to be destroyed by the accumulation of fibrillar amyloid deposits consisting primarily of a protein known as islet amyloid polypeptide (IAPP) or amylin. Specifically the islet is depleted in beta-cell mass due to beta-cell apoptosis and islet amyloid. In vitro studies have shown that amyloidogenic human IAPP is toxic to cultured beta-cells (Lorenzo, A., et al., Nature 368:756-760, 1994). In monkey's islet amyloid deposition has been temporally correlated with the onset of hyperglycemia (Howard, C. F. Diabetologia 29:301-306, 1986). A transgenic mouse model is available with increased human IAPP transgene expression which leads to beta-cell apoptosis and diabetes in the model animal (Matveyenkp A V and Butler P C. ILAR J. 47(3):225-233, 2006). Inhibiting or reducing such IAPP amyloid fibril formation, deposition, accumulation and persistence may be beneficial for the treatments for type 2 diabetes.

Discovery and identification of new compounds or agents as potential therapeutics to arrest amyloid formation, deposition, accumulation and/or persistence that occurs in IAPP amyloid disease, such as type 2 diabetes, are sought.

SUMMARY OF THE INVENTION

This invention relates to bis-dihydroxyaryl compounds and pharmaceutically acceptable salts thereof. The compounds are useful in the treatment of IAPP amyloid disease, such as type 2 diabetes.

The compounds are:
compounds of the formula:

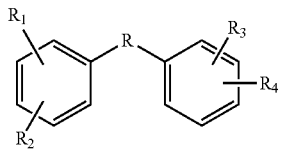

where R is selected from —C(O)NR', sulfonamide, a five membered heteroaryl, tricycloalkyl or pharmaceutically acceptable esters or salts thereof, where R' is selected from H or $CH_3$, and where $R_1$, $R_2$, $R_3$, and $R_4$ are OH, and when R is —C(O)NR' and R' is H and $R_1$ and $R_2$ are in the 3,4-position, then $R_3$ and $R_4$ are not; or when $R_3$ and $R_4$ are in the 3,4-position, then $R_1$ and $R_2$ are not.

Also provided are any pharmaceutically-acceptable derivatives, including salts, esters, enol ethers or esters, acetals, ketals, orthoesters, hemiacetals, hemiketals, solvates, hydrates or prodrugs of the compounds. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl)aminomethane, alkali metal salts, such as but not limited to lithium, potassium and sodium, alkali earth metal salts, such as but not limited to barium, calcium and magnesium, transition metal salts, such as but not limited to zinc and other metal salts, such as but not limited to sodium hydrogen phosphate and disodium phosphate, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates.

Pharmaceutical formulations for administration by an appropriate route and means containing effective concentrations of one or more of the compounds provided herein or pharmaceutically acceptable derivatives, such as salts, esters, enol ethers or esters, acetals, ketals, orthoesters, hemiacetals, hemiketals, solvates, hydrates or prodrugs, of the compounds that deliver amounts effective for the treatment of amyloid diseases, are also provided.

The formulations are compositions suitable for administration by any desired route and include solutions, suspensions, emulsions, tablets, dispersible tablets, pills, capsules, powders, dry powders for inhalation, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Methods using such compounds and compositions for disrupting, disaggregating and causing removal, reduction or clearance of IAPP amyloid are provided thereby providing new treatments for type 2 diabetes.

Also provided are methods for treatment, prevention or amelioration of one or more symptoms of amyloid diseases or amyloidoses, including but not limited to diseases associated with the formation, deposition, accumulation, or persistence of IAPP amyloid fibrils.

Also provided are methods for treatment, prevention or amelioration of one or more symptoms of type 2 diabetes. In one embodiment, the methods inhibit or prevent IAPP fibril formation, inhibit or prevent IAPP fibril growth, and/or cause disassembly, disruption, and/or disaggregation of preformed IAPP fibrils and IAPP-associated protein deposits.

DETAILED DESCRIPTION OF THE INVENTION

Definitions

In this application, the following terms shall have the following meanings, without regard to whether the terms are used variantly elsewhere in the literature or otherwise in the known art.

As used herein "Amyloid diseases" or "amyloidoses" are diseases associated with the formation, deposition, accumulation, or persistence of IAPP amyloid fibrils such as type 2 diabetes.

"Fibrillogenesis" refers to the formation, deposition, accumulation and/or persistence of IAPP amyloid fibrils, filaments, inclusions, deposits, or the like.

"Inhibition of fibrillogenesis" refers to the inhibition of formation, deposition, accumulation and/or persistence of such a IAPP amyloid fibrils.

"Disruption of fibrils or fibrillogenesis" refers to the disruption of pre-formed IAPP amyloid fibrils, that usually exist in a pre-dominant β-pleated sheet secondary structure. Such disruption by compounds provided herein may involve marked reduction or disassembly of amyloid as assessed by various methods such as Thioflavin T fluorometry, Congo red binding.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use or for human pharmaceutical use. Such excipients may be solid, liquid, semisolid, or, in the case of an aerosol composition, gaseous.

A "therapeutically effective amount" means the amount that, when administered to a subject or animal for treating a disease, is sufficient to affect the desired degree of treatment, prevention or symptom amelioration for the disease. A "therapeutically effective amount" or a "therapeutically effective dosage" in certain embodiments inhibits, reduces, disrupts, disassembles IAPP amyloid fibril formation, deposition, accumulation and/or persistence, or treats, prevents, or ameliorates one or more symptoms of a disease associated with these conditions, such as type 2 diabetes, in a measurable amount in one embodiment, by at least 20%, in other embodiment, by at least 40%, in other embodiment by at least 60%, and in still other embodiment by at least 80%, relative to an untreated subject. Effective amounts of a compound provided herein or composition thereof for treatment of a mammalian subject are about 0.1 to about 1000 mg/Kg of body weight of the subject/day, such as from about 1 to about 100 mg/Kg/day, in other embodiment, from about 10 to about 500 mg/Kg/day. A broad range of disclosed composition dosages are believed to be both safe and effective.

The term "sustained release component" is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiological solvents may be formulated for administration by inhalation or insufflation (either through the mouth or the nose) or oral, buccal, parenteral, or rectal administration, as examples.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment may also include prophylactic treatment and inhibiting the disease slowing or arresting its development to providing relief from the symptoms or side-effects of the disease (including palliative treatment), and relieving the disease (causing regression of the disease), such as by disruption of pre-formed IAPP amyloid fibrils.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Chemical structures for some of the compounds of this invention are shown. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3,4-dihydroxyphenyl)-3,4-dihydroxybenzamide"). However, the names used are often explicitly equated to chemical structures, and are believed to be readily understood by a person of ordinary skill in the art.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield, what those skilled in the art would identify as a single sharp-peak band.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl imidazole, triazole and pyrazole.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl.

As used herein, "dialkylaminocarbonyl" refers to —C(O)NR'R in which R' and R are each independently alkyl, including lower alkyl; "carboxamide" refers to groups of formula —NR'COR in which R' and R are each independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S(=O)—(CRR)$_m$—, and —(CRR)$_n$—S(=O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C≡C—(CH$_2$)$_n$—C=C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —NC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO$_2$NHNH—. "Hydrazide" refers to the divalent group —C(O)NHNH—. "Azo" refers to the divalent group —N=N—. "Hydrazinyl" refers to the divalent group —NH—NH—.

As used herein, "sulfonamide" refers to —RSO$_2$NH$_2$— a sulfone group connected to an amine group.

As used herein, "imidazole" refers to a heterocyclic aromatic organic compound having a general formula of $C_3H_4N_2$.

As used herein, "triazole" refers to either one of a pair of isomeric chemical compounds with molecular formula of $C_2H_3N_3$.

As used herein, "pyrazole" refers to a heterocyclic 5-membered ring composed of three carbons and two nitrogen atoms in adjacent positions.

As used herein, "adamantane" refers to a tricycloalkyl having a general formula of $C_{10}H_{16}$.

Where the number of any given substituent is not specified (e.g., haloalkyl), there may be one or more substituents present. For example, "haloalkyl" may include one or more of the same or different halogens. As another example, "$C_{1-3}$ alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

Compounds of the Invention

The compounds of this invention are:

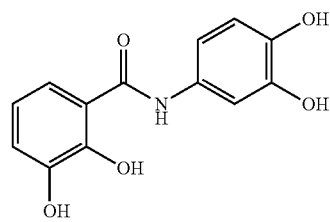

(Compound 1)

2,3 dihydroxybenzoic acid 3,4 dihydroxyanilide,

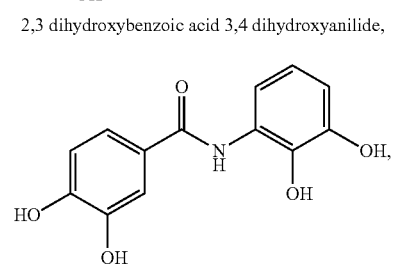

(Compound 2)

3,4 dihydroxybenzoic acid 2,3 dihydroxyanilide

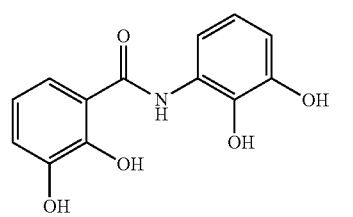

(Compound 3)

2,3 dihydroxybenzoic acid 2,3 dihydroxyanilide,

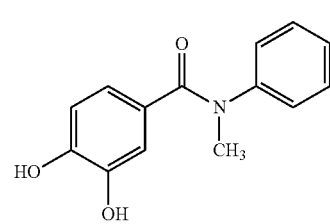

(Compound 4)

3,4 dihydroxybenzoic acid 3,4 dihydroxy N-methyl anilide,

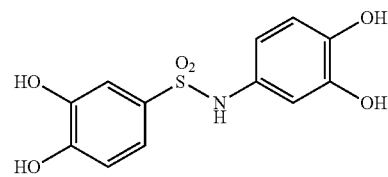

(Compound 5)

3,4 dihydroxybenzenesulfonic acid 3,4 dihydroxysulfonamide,

-continued

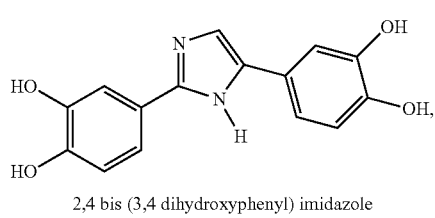

2,4 bis (3,4 dihydroxyphenyl) imidazole (Compound 6)

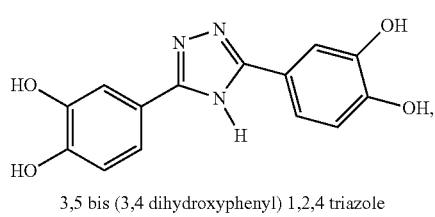

3,5 bis (3,4 dihydroxyphenyl) 1,2,4 triazole (Compound 7)

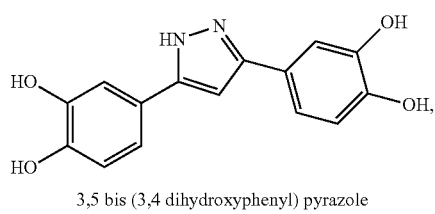

3,5 bis (3,4 dihydroxyphenyl) pyrazole (Compound 8)

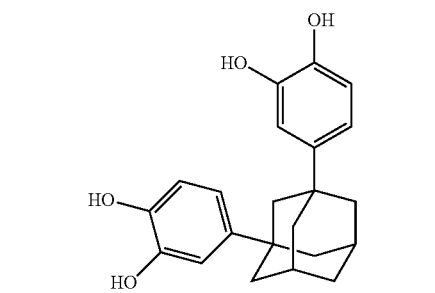

1,3 bis (3,4 dihydroxyphenyl) adamantane, (Compound 9)

Synthesis of the Compounds of the Invention

The compounds of this invention may be prepared by methods generally known to the person of ordinary skill in the art, having regard to that knowledge and the disclosure of this application including Examples 1-5.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The compounds provided herein can be used as such, be administered in the form of pharmaceutically acceptable salts derived from inorganic or organic acids, or used in combination with one or more pharmaceutically acceptable excipients. The phrase "pharmaceutically acceptable salt" means those salts which are, within the scope of sound medical judgment, suitable for use in contact with the tissues without undue toxicity, irritation, allergic response, and the like, and are commensurate with a reasonable benefit/risk ratio. Pharmaceutically acceptable salts are well known in the art. The salts can be prepared either in situ during the final isolation and purification of the compounds provided herein or separately by reacting the acidic or basic drug substance with a suitable base or acid respectively. Typical salts derived from organic or inorganic acids salts include, but are not limited to hydrochloride, hydrobromide, hydroiodide, acetate, adipate, alginate, citrate, aspartate, benzoate, bisulfate, gluconate, fumarate, hydroiodide, lactate, maleate, oxalate, palmitoate, pectinate, succinate, tartrate, phosphate, glutamate, and bicarbonate. Typical salts derived from organic or inorganic bases include, but are not limited to lithium, sodium, potassium, calcium, magnesium, ammonium, monoalkylammonium such as meglumine, dialkylammonium, trialkylammonium, and tetralkylammonium.

Actual dosage levels of active ingredients and the mode of administration of the pharmaceutical compositions provided herein can be varied in order to achieve the effective therapeutic response for a particular patient. The phrase "therapeutically effective amount" of the compound provided herein means a sufficient amount of the compound to treat disorders, at a reasonable benefit/risk ratio applicable to any medical treatment. It will be understood, however, that the total daily usage of the compounds and compositions of the provided will be decided by the attending physician within the scope of sound medical judgment. The total daily dose of the compounds provided herein may range from about 0.1 to about 1000 mg/kg/day. For purposes of oral administration, doses can be in the range from about 1 to about 500 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion of the specific compound employed, drugs used in combination or coincidental with the specific compound employed; and the like.

The compounds provided can be formulated together with one or more non-toxic pharmaceutically acceptable diluents, carriers, adjuvants, and antibacterial and antifungal agents such as parabens, chlorobutanol, phenol, sorbic acid, and the like. Proper fluidity can be maintained, for example, by the use of coating materials such as lecithin, by the maintenance of the required particle size in the case of dispersions, and by the use of surfactants. In some cases, in order to prolong the effect of the drug, it is desirable to decrease the rate of absorption of the drug from subcutaneous or intramuscular injection. This can be accomplished by suspending crystalline or amorphous drug substance in a vehicle having poor water solubility such as oils. The rate of absorption of the drug then depends upon its rate of dissolution, which, in turn, may depend upon crystal size and crystalline form. Prolonged absorption of an injectable pharmaceutical form can be achieved by the use of absorption delaying agents such as aluminum monostearate or gelatin.

The compound provided herein can be administered enterally or parenterally in solid or liquid forms. Compositions suitable for parenteral injection may comprise physiologically acceptable, isotonic sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances.

The compounds provided herein can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds provided herein may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

In one embodiment, the compounds are formulated in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of an IAPP amyloid disease. Compositions for rectal or vaginal administration are preferably suppositories which can be prepared by mixing the compounds provided herein with suitable non-irritating excipients or carriers such as cocoa butter, polyethylene glycol or a suppository wax which are solid at room temperature but liquid at body temperature and therefore melt in the rectum or vaginal cavity and release the active compound.

Compounds provided herein can also be administered in the form of liposomes. Methods to form liposomes are known in the art (Prescott, Ed., *Methods in Cell Biology* 1976, Volume XIV, Academic Press, New York, N.Y.) As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound provided herein, stabilizers, preservatives, excipients and the like. The preferred lipids are natural and synthetic phospholipids and phosphatidyl cholines (lecithins).

The compounds provided herein can also be administered in the form of a 'prodrug' wherein the active pharmaceutical ingredients, are released in vivo upon contact with hydrolytic enzymes such as esterases and phophatases in the body. The term "pharmaceutically acceptable prodrugs" as used herein represents those prodrugs of the compounds provided herein, which are, within the scope of sound medical judgment, suitable for use in contact with the tissues without undue toxicity, irritation, allergic response, and the like, commensurate with a reasonable benefit/risk ratio, and effective for their intended use. A thorough discussion is provided in T. Higuchi and V. Stella (Higuchi, T. and Stella, V. Pro-drugs as Novel Delivery Systems, V. 14 of the A.C.S. Symposium Series; Edward B. Roche, Ed., *Bioreversible Carriers in Drug Design* 1987, American Pharmaceutical Association and Pergamon Press), which is incorporated herein by reference.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Sustained Release Formulations

The invention also includes the use of sustained release formulations to deliver the compounds of the present invention to the desired target (i.e. brain or systemic organs) at high circulating levels (between $10^{-9}$ and $10^{-4}$ M) are also disclosed. In a preferred embodiment for the treatment of Alzheimer's or Parkinson's disease, the circulating levels of the compounds is maintained up to $10^{-7}$ M. The levels are either circulating in the patient systemically, or in a preferred embodiment, present in brain tissue, and in a most preferred embodiments, localized to the β-amyloid or α-synuclein fibril deposits in brain or other tissues.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material, preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

Evaluation of the Activity of the Compounds

The biological activity of the compounds provided herein as disruptors/inhibitors of IAPP amyloid protein fibrils, was assessed by determining the efficacy of the compounds to cause a disassembly/disruption of pre-formed IAPP amyloid fibrils. In one study, Thioflavin T fluorometry was used to determine the effects of the compounds, and of EDTA or PD-68 (as a negative control). In this assay Thioflavin T binds specifically to fibrillar amyloid, and this binding produces a fluorescence enhancement at 485 nm that is directly proportional to the amount of fibrils present. The higher the fluorescence, the greater the amount of fibrils present (Naki et al, *Lab. Invest.* 65:104-110, 1991; Levine III, *Protein Sci.* 2:404-410, 1993; *Amyloid: Int. J. Exp. Clin. Invest.* 2:1-6, 1995).

In the Congo red binding assay the ability of a given test compound to alter amyloid binding to Congo red was quantified. In this assay, IAPP fibrils and test compounds were incubated for 3 days and then vacuum filtered through a 0.2 µm filter. The amount of IAPP fibrils retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic IAPP fibrils.

Combination Therapy

In another embodiment, the compounds may be administered in combination, or sequentially, with another therapeutic agent. Such other therapeutic agents include those known for treatment, prevention, or amelioration of one or more symptoms of type 2 diabetes.

Methods of Use of the Compounds and Compositions

The compounds and compositions provided herein are useful in methods of treatment, prevention, or amelioration of one or more symptoms of LAPP amyloid diseases or disorders, including but not limited to diseases associated with the formation, deposition, accumulation, or persistence of IAPP amyloid fibrils. In certain embodiments, the compounds and compositions provided herein are used for treatment, prevention, or amelioration of one or more symptoms of diseases including, type 2 diabetes.

The following non-limiting Examples are given by way of illustration only and are not considered a limitation of this invention, many apparent variations of which are possible without departing from the spirit or scope thereof.

EXAMPLES

General Experimental Procedures

All solvents were distilled before use and were removed by rotary evaporation at temperatures up to 35° C. Merck silica gel 60, 200-400 mesh, 40-63 µm, was used for silica gel flash chromatography. TLC was carried out using Merck DC-plastikfolien Kieselgel 60 F254, first visualised with a UV lamp, and then by dipping in a vanillin solution (1% vanillin, 1% $H_2SO_4$ in EtOH), and heating. Mass spectra were recorded on a Kratos MS-80 instrument. NMR spectra, at 25° C., were recorded at 500 or 300 MHz for $^1H$ and 125 or 75 MHz for $^{13}C$ on Varian INOVA-500 or VXR-300 spectrometers. Chemical shifts are given in ppm on the δ scale referenced to the solvent peaks: $CHCl_3$ at 7.25 and $CDCl_3$ at 77.0 ppm or $(CH_3)_2CO$ at 2.15 and $(CD_3)_2CO$ at 30.5 ppm or $CH_3OD$ at 3.30 and $CD_3OD$ at 39.0 ppm.

HPLC Conditions

Samples were analysed using an Agilent HP1100 instrument, operated with EzChrom Elite software, and fitted with a C18 column (Phenomenex Prodigy 5 µm 100 A, 250×4.6 mm) with a guard column (Phenomenex ODS 4×3 mm, 5 µm) held at 30° C. Peaks were detected at 280 nm. The mobile phase was acetonitrile in water (with 0.1% TFA): $t_0$=11%, $t_{20}$=11%, $t_{30}$=100%, $t_{31}$=11%, $t_{40}$=11%. The flow rate was 1 mL/min and the injection volume of 5 µL.

Example 1

Synthesis of Sulfonamide 2

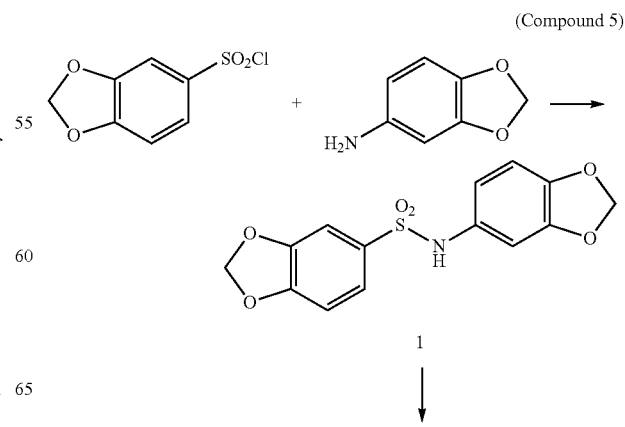

-continued

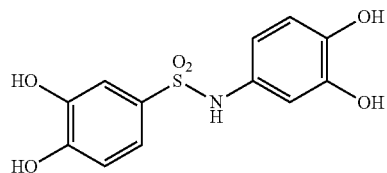

2
3,4 dihydroxybenzenesulfonic acid
3,4 dihydroxysulfonamide

Synthesis of the sulfonamide 2 was accomplished by reaction of 3,4-methylenedioxybenzenesulfonyl chloride (prepared from 1,2-methylenedioxybenzene (Tao, E. V. P.; Miller, W. D. U.S. Pat. No. 5,387,681. 1995)) with 3,4-methylenedioxyaniline to give the sulfonamide 1 in good yield. Deprotection with boron tribromide under standard conditions gave the free phenolic sulfonamide in reasonable yield.

To a stirred solution of 1,3-benzodioxole-5-sulfonyl chloride (Tao, E. V. P.; Miller, W. D. U.S. Pat. No. 5,387,681. 1995) (1 g) in dichloromethane (DCM) (10 ml) was added a solution of 3,4-methylenedioxyaniline (0.62 g) in dichloromethane (10 ml) followed by pyridine (1 ml). The mixture was refluxed for 2 hours, cooled, diluted with dichloromethane (150 ml), washed with aqueous HCl (1M, 2×100 ml), dried, then evaporated in vacuo to give the crude product as a brown gum. Purification by column chromatography over silica gel eluting with 5-10% ethyl acetate in dichloromethane gave the pure sulphonamide 1 as a pale brown gum (1.34 g, 92%). Crystallisation from 95% ethanol gave the product as pale brown crystals.

HPLC 29.6 minutes.

$^1$H NMR ((CD$_3$)$_2$CO) 8.75 (1H, s), 7.39 (2H, dd, J 2, 9 Hz), 7.24 (1H, d, J=2 Hz), 7.02 (1H, d, J=9 Hz), 6.86 (1H, d, J=2 Hz), 6.81 (1H, d, J=9 Hz), 6.72 (2H, dd, J 2, 9 Hz), 6.23 (2H, s) and 6.06 (2H, s).

HREIMS Found, 344.0201; MNa$^+$, C$_{14}$H$_{11}$NNaO$_6$S requires 344.0199.

To a solution of the sulphonamide 1 (0.7 g) in dry DCM (50 ml) was added boron tribromide (0.5 ml) and the mixture left at room temperature for 3 hours. Methanol (dropwise then 5 ml) was added carefully then the reaction left at room temperature for 24 hours. The mixture was evaporated in vacuo to 1 ml, then more methanol (20 ml) was added, this was repeated four times, then the solvents were removed by evaporation in vacuo.

Purification by column chromatography over silica gel eluting with 0-20% methanol in chloroform gave the product as a pale brown gum. Further purification over C-18 reverse phase silica eluting with 0-50% acetonitrile in water, followed by freeze drying, gave the pure product 2 as a light brown powder (295 mg, 45%).

HPLC 12.9 minutes 95%

$^1$HNMR (CD$_3$OD) 7.05 (1H, d, J=2 Hz), 7.03 (2H, dd, J 2, 9 Hz), 6.76 (1H, d, J=9 Hz), 6.57 (1H, d, J=2 Hz), 6.56 (1H, d, J=9 Hz) and 6.31 (2H, dd, J 2, 9 Hz).

HREIMS Found, 296.0241, M$^-$, C$_{12}$H$_{10}$NO$_6$S requires, 296.0234.

Example 2

Synthesis of Imidazole 4

(Compound 6)

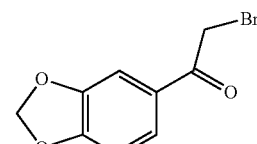

+

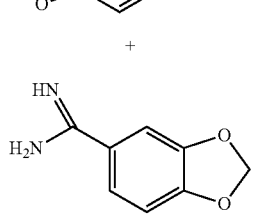

→

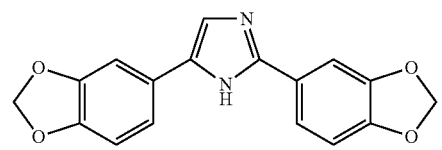

3

↓

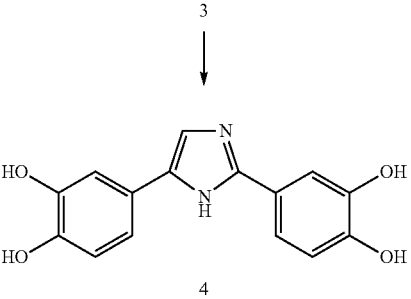

4

2,4 bis (3,4 dihydroxyphenyl) imidazole

The imidazole ring was formed according to the method described by Li et al. (Li et al. Organic Process Research and Development 2002, 6, 682-3) from the amidinobenzene, formed from piperonylonitrile (Thurkauf et al. J Med. Chem. 1995, 38 (12), 2251-2255) and the bromoketone (Castedo et al. Tetrahedron 1982, 38 (11), 1569-70) formed from 3,4-methylenedioxyacetophenone according to the method described by Lee et al. (Korean Chem. Soc. 2003, 24 (4), 407-408). Deprotection with boron tribromide under standard conditions gave the free phenolic imidazole in good yield.

According to the process described by Li, a mixture of 3-amidinobenzene (Thurkauf et al. J Med. Chem. 1995, 38 (12), 2251-2255) (0.5 g, 3 mmol) and potassium bicarbonate (1.20 g, 12 mmol) in tetrahydrofuran (THF) (16 ml) and water (4 ml) was heated vigorously at reflux. Bromoketone (Castedo et al. Tetrahedron 1982, 38 (11), 1569-70; and Lee et al. Korean Chem. Soc. 2003, 24 (4), 407-408) (0.729 g, 3 mmol) in THF (4 ml) was added over 30 minutes and reflux was maintained for a further 2 hours. The THF was then removed by evaporation in vacuo and the residue extracted into ethyl acetate, dried and evaporated in vacuo to give the crude product as a brown solid. Crystallisation from 95% ethanol gave the pure imidazole 3 as a pale yellow crystalline solid (0.54 g, 58%).

HPLC 27.9 minutes. NMR ((CD$_3$)$_2$CO) 7.45-7.70 (5H, m), 7.02 (1H, d, J=9 Hz), 6.95 (1H, d, J=9 Hz), 6.15 (2H, s) and 6.09

(2H, s) HREIMS Found, 309.0875; MH$^+$, C$_{17}$H$_{12}$N$_2$O$_4$ requires, 309.0870.

To a solution of the imidazole 3 (0.5 g) in dry DCM (50 ml) was added boron tribromide (1.0 ml) and the mixture left at room temperature for 3 hours. Methanol (dropwise then 5 ml) was added carefully then the reaction left at room temperature for 24 hours. The mixture was evaporated in vacuo to 1 ml, then more methanol (30 ml) was added, this was repeated four times, then the solvents were removed by evaporation in vacuo.

Purification by column chromatography over silica gel eluting with 0-20% methanol in chloroform gave the product 4 as a pale brown solid (0.27 g, 58%).

HPLC 16.3 minutes 99%

$^1$H NMR (CD$_3$OD) 7.59 (1H, s), 7.36 (1H, d, J=2 Hz), 7.31 (2H, dd, J 2, 9 Hz), 7.16 (1H, d, J=2 Hz), 7.10 (2H, dd, J 2, 9 Hz), 6.98 (1H, d, J=9 Hz) and 6.88 (1H, d, J=9 Hz).

HREIMS Found, 285.0873; MH$^+$, C$_{15}$H$_{13}$N$_2$O$_4$ requires 285.0870.

Example 3

Synthesis of Triazole 7

According to the process described by Bentiss (Bentiss et al. J Heterocyclic Chem. 1999, 36, 149-152) a mixture of aromatic nitrile (1 g), hydrazine hydrate (1 g) and hydrazine hydrochloride (0.5 g) in solution in ethylene glycol (5 ml) was heated to 130° C. for 5 hours. The solution was cooled then diluted with water (7 ml), the solid product was filtered, washed with DCM then dried to give the crude product. Recrystalisation from methanol gave the pure 4-aminotriazole 5, as a pale yellow solid (0.65 g, 66%).

HPLC 27.0 minutes.

$^1$H NMR ((CD$_3$)$_2$CO) 7.62 (2H, dd, J 2, 9 Hz), 7.42 (2H, d, J=2 Hz), 6.94 (2H, d, J=9 Hz), 6.15 (2H, s) and 5.93 (4H, s).

HREIMS Found, 325.0937; MH$^+$, C$_{16}$H$_{13}$N$_4$O$_4$ requires 325.0931.

According to the process described by Bentiss (Bentiss et al. J. Heterocyclic Chem. 2002, 39, 93-96) to a stirred solution of amino triazole 5 (0.5 g) in an aqueous solution of hypophosphorus acid (50%, 5 ml) a solution of sodium nitrite (0.6 g) in water (1.5 ml) was added slowly. The mixture was stirred at room temperature for a further hour then the pale orange precipitate was collected, washed with water and dried to give the triazole 6 (0.38, 80%).

HPLC 29.48 minutes.

$^1$H NMR ((CD$_3$)$_2$CO) 7.81 (2H, dd, J 2, 9 Hz), 7.70 (2H, d, J=2 Hz), 7.10 (2H, d, J=9 Hz) and 6.20 (4H, s). HREIMS Found, 310.0818; C$_{16}$H$_{12}$N$_3$O$_4$ requires 310.0822.

To a solution of the triazole 6 (0.5 g) in dry DCM (50 ml) was added boron tribromide (1.0 ml) and the mixture left at room temperature for 3 hours. Methanol (dropwise then 5 ml) was added carefully then the reaction left at room temperature for 24 h. The mixture was evaporated in vacuo to 1 ml, then more methanol (30 ml) was added, this was repeated four times, then the solvents were removed by evaporation in vacuo.

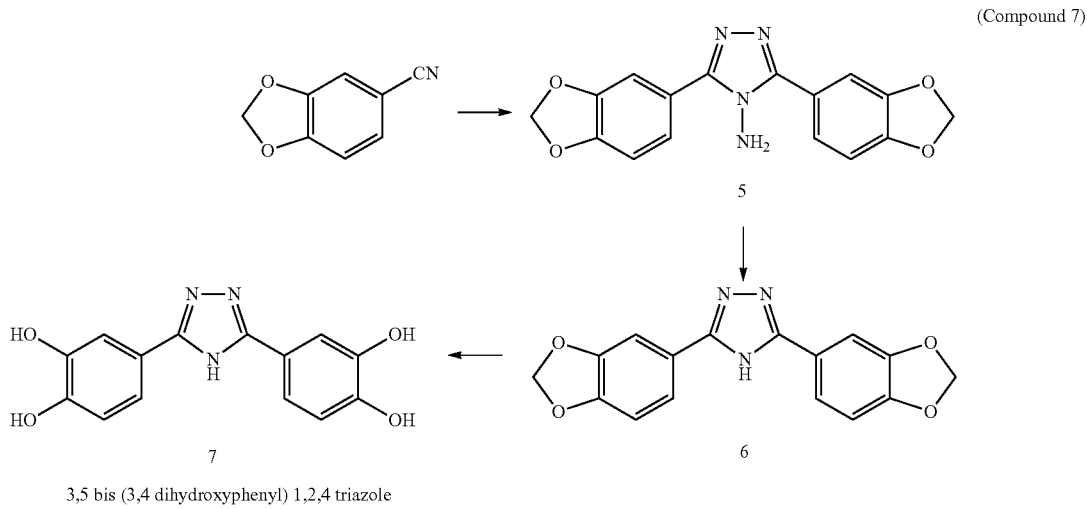

3,5 bis (3,4 dihydroxyphenyl) 1,2,4 triazole

The 4-aminotriazole ring was formed by a dimerization reaction of piperonylonitrile according to the method described by Bentiss (Bentiss et al. J Heterocyclic Chem. 1999, 36, 149-152) and then deamination was carried out according to the method described by Bentiss (Bentiss et al. J. Heterocyclic Chem. 2002, 39, 93-96.) to give the triazole 6 in good yield. Deprotection with boron tribromide under standard conditions gave the free phenolic triazole 7 in good yield.

Purification by column chromatography over silica gel eluting with 0-20% methanol in chloroform gave the product 7 as a pale brown solid (0.24 g, 52%).

HPLC 16.1 minutes 97%

$^1$H NMR (CD$_3$OD) 7.46 (2H, d, J=2 Hz), 7.41 (2H, dd, J 2, 9 Hz), 7.15 (1H, s) and 6.96 (2H, d, J=9 Hz).

HREIMS Found, 286.0815; MH$^+$, C$_{14}$H$_{12}$N$_3$O$_4$ requires 286.0822.

Example 4

Synthesis of Pyrazole 9

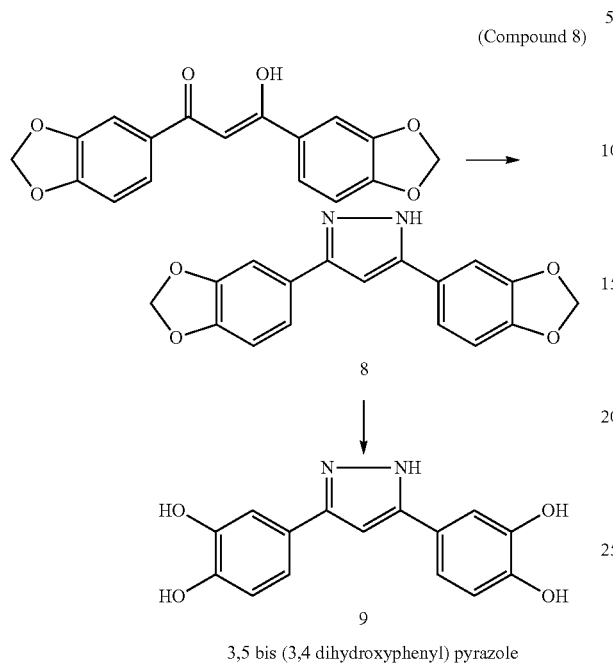

3,5 bis (3,4 dihydroxyphenyl) pyrazole

Reaction of the 1,3-diketone (Lopez et al. Planta Med. 1998, 64 (1), 76-77) (prepared according to the method described by Choshi et al. (Chem. Pharm. Bull. 1992, 40 (4), 1047-1049) with hydrazine hydrate according to the method described by Fink et al. (Chemistry and Biology 1999, 6, 205-219) gave the pyrazole S in good yield. Deprotection with boron tribromide under standard conditions gave the free phenolic pyrazole 9 in good yield.

According to the method described by Fink et al. (Chemistry and Biology 1999, 6, 205-219) a suspension of the diketone (Choshi et al. Chem. Pharm. Bull. 1992, 40 (4), 1047-1049 and Lopez et al. Planta Med. 1998, 64 (1), 76-77) (1 g) and hydrazine HCl (1 g, 5 equivs) in DMF/THF (3:1, 12 ml) was heated to reflux for 24 h. Water was added and the mixture extracted into dichloromethane, dried and evaporated in vacuo to give the crude product 8 as a yellow solid. Purification by column chromatography over silica gel eluting with 0-20% ethyl acetate in dichloromethane gave the pyrazole 8 as a pale yellow solid (0.49 g, 50%).

HPLC 30.3 minutes
$^1$H NMR ((CD$_3$)$_2$CO) 7.47 (2H, dd, J 2, 9 Hz), 7.46 (2H, d, J=2 Hz), 7.04 (1H, s), 7.02 (2H, d, J=9 Hz) and 6.14 (4H, s).
HREIMS Found, 309.0859; MH$^+$, C$_{17}$H$_{13}$N$_2$O$_4$ requires 309.0870.

To a solution of the pyrazole 8 (0.46 g) in dry DCM (50 ml) was added boron tribromide (0.4 ml) and the mixture left at room temperature for 3 hours. Methanol (dropwise then 5 ml) was added carefully then the reaction left at room temperature for 24 hours. The mixture was evaporated in vacuo to 1 ml, then more methanol (30 ml) was added, this was repeated four times, then the solvents were removed by evaporation in vacuo.

Purification by column chromatography over silica gel eluting with 0-20% methanol in chloroform gave the pyrazole 9 as a pale yellow solid. (0.285 g, 67%).

HPLC 25.9 minutes 98%
$^1$H NMR (CD$_3$OD) 7.26 (2H, d, J=2 Hz), 7.22 (2H, dd, J 2, 9 Hz), 7.15 (1H, s) and 6.93 (2H, d, J=9 Hz).

HREIMS Found, 285.0879; C$_{15}$H$_{13}$N$_2$O$_4$ requires, 285.0870.

Example 5

Synthesis of Adamantane 10

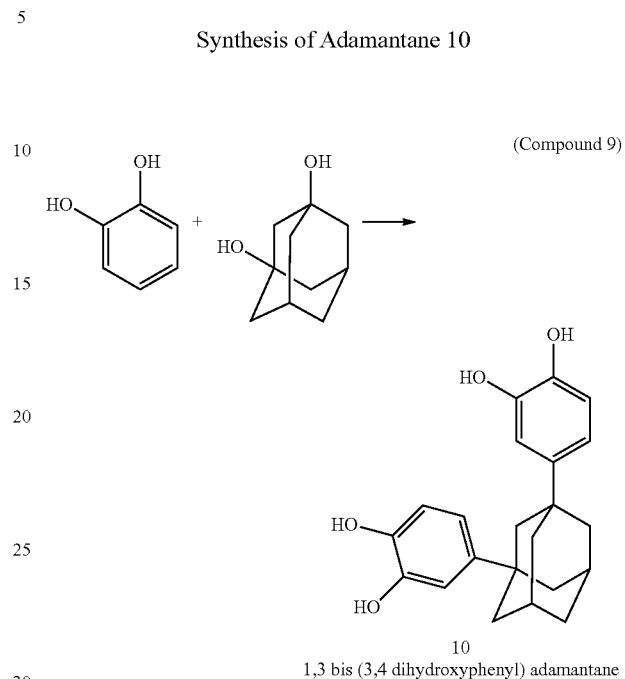

1,3 bis (3,4 dihydroxyphenyl) adamantane

Reaction of catechol with 1,3-adamantane-diol according to the method described by Lu et al (Lu et al. J Med Chem 2005, 48 (14), 4576-4585) gave the adduct 10 in reasonable yield.

According to the method described by Lu a solution of catechol (1.0 g) and adamantane diol (0.5 g) in methane-sulfonic acid (2 ml) was heated to 80° C. for 3 hours, then left at room temperature overnight. Water was added and the mixture extracted into 10% methanol in chloroform which was dried and evaporated in vacuo to give a white solid. Purification by column chromatography over silica gel eluting with 0-20% methanol in chloroform gave the product as a white solid. Crystallisation from diethyl ether/40% petroleum ether then gave the pure product 10 as a white crystalline solid (210 mg, 20%).

HPLC 29.8 minutes 98%
$^1$H NMR (CD$_3$OD) 6.82 (2H, t, J=1.5 Hz), 6.68 (4H, d, J=1.5 Hz), 2.22 (2H, bs), 1.87 (8H, m) and 1.77 (2H, bs).
HREIMS Found, 387.1369; MCl$^-$, C$_{22}$H$_{24}$ClO$_4$ requires, 387.1369.

Example 6

Compounds of this Invention are Potent Disrupters of IAPP Type 2 Diabetes Amyloid Fibrils (Amylin)

The compounds prepared in the preceding Examples were found to also be potent disruptors/inhibitors of Type 2 Diabetes fibrils (IAPP/amylin), also considered an amyloid fibril. In a set of studies, the efficacy of the compounds to cause a disassembly/disruption of pre-formed fibrils of Type 2 Diabetes (amylin or IAPP fibrils) was analyzed.

Part A—Thioflavin T Fluorometry Data

In one study, Thioflavin T fluorometry was used to determine the effects of the compounds compared to DP-68 (a negative control), or for example, EDTA which could just as effectively serve as a negative control. In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., *Lab. Invest.* 65:104-110, 1991; Levine III, *Protein Sci.* 2:404-410, 1993; *Amyloid: Int. J. Exp. Clin. Invest.* 2:1-6, 1995). The same premise is applied to Amylin/IAPP fibrils.

In this study, 30 μg of pre-fibrillized Amylin/IAPP (Bachem Inc) was incubated at 37° C. for 3 days either alone, or in the presence of one of the compounds or negative control (at Amylin/IAPP:test compound weight ratios of 1:1, 1:0.1, 1:0.01 or 1:0.001). Following 3-days of co-incubation, 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank.

The results of the 3-day incubations are presented below in Table 1. For example, whereas DP-68 (negative control) caused no significant inhibition of Amylin/IAPP fibrils at all concentrations tested, the compounds tested all caused a dose-dependent disruption/disassembly of preformed Amylin/IAPP fibrils. The most efficacious compounds to disrupt pre-formed Amylin/IAPP fibrils appeared to be compounds #6, 4, 1, 3 and 5. For example, compound #6 caused a significant ($p<0.01$) 96.3±0.76% inhibition when used at an Amylin/IAPP:test compound wt/wt ratio of 1:0.1, and a 68.9±3.33% disruption when used at an Amylin/IAPP:compound wt/wt ratio of 1:0.01. Compound #4 caused a significant ($p<0.01$) 95.4±0.23% inhibition when used at an Amylin/IAPP:test compound wt/wt ratio of 1:0.1, and a 57.4±1.61% disruption when used at an Amylin/IAPP:compound wt/wt ratio of 1:0.01. With an Amylin/IAPP:test compound wt/wt ratio of 1:0.1, compound #1 caused a 95.1±0.48% disruption, and at 1:0.01 caused a 60.9±0.61% disruption. With an Amylin/IAPP:test compound wt/wt ratio of 1:0.1, compound #3 caused a 94.5±0.91% disruption, and at 1:0.01 caused a 51.7±3.56% disruption. Compound #5 at an Amylin/IAPP:test compound wt/wt ratio of 1:0.1 caused a 93.7±1.13% disruption and at 1:0.01 caused a 56.71-0.4% disruption. This study indicated that the compounds of this invention are potent disruptors/inhibitors of Type 2 Diabetes type Amylin/IAPP fibrils, and usually exert their effects in a dose-dependent manner.

TABLE 1

Thioflavin T fluorometry data - disruption of Amylin/IAPP Type 2 Diabetes fibrils
% Inhibition Amylin/IAPP (result ± S.D.) at Amylin/IAPP:test compound wt/wt ratio given

| Test Compound # | 1:1 | 1:0.1 | 1:0.01 | 1:0.001 |
|---|---|---|---|---|
| (control) | 14.0 ± 1.30 | 11.0 ± 0.96 | 0.0 ± 6.33 | 1.1 ± 6.97 |
| 1 | 98.5 ± 0.26 | 95.1 ± 0.48 | 60.9 ± 0.61 | 14.3 ± 3.56 |
| 2 | 99.4 ± 1.69 | 92.6 ± 0.84 | 52.9 ± 4.36 | 5.1 ± 4.57 |
| 3 | 99.3 ± 0.6 | 94.5 ± 0.91 | 51.7 ± 3.56 | 5.0 ± 6.78 |
| 4 | 100.0 ± 0.09 | 95.4 ± 0.23 | 57.4 ± 1.61 | 9.8 ± 7.47 |
| 5 | 99.7 ± 0.38 | 93.7 ± 1.13 | 56.7 ± 0.40 | 14.1 ± 1.62 |
| 6 | 100.0 ± 0.26 | 96.3 ± 0.76 | 68.9 ± 3.33 | 17.2 ± 4.22 |
| 7 | 99.8 ± 0.31 | 89.7 ± 0.54 | 41.4 ± 2.13 | 4.6 ± 4.34 |
| 8 | 99.0 ± 1.05 | 91.2 ± 0.76 | 48.4 ± 0.31 | 8.1 ± 1.54 |
| 9 | 97.6 ± 0.31 | 88.5 ± 0.31 | 36.6 ± 3.55 | 4.3 ± 2.29 |

Part B: Congo Red Binding Data

In the Congo red binding assay the ability of a test compound to alter Amylin/IAPP binding to Congo red is quantified. In this assay, Amylin/IAPP and test compounds were incubated for 3 days and then vacuum filtered through a 0.2 μm filter. The amount of Amylin/IAPP retained in the filter was then quantitated following staining of the filter with Congo red. After appropriate washing of the filter, any lowering of the Congo red color retained on the filter in the presence of the test compound (compared to the Congo red staining of the Amylin/IAPP protein in the absence of the test compound) was indicative of the test compound's ability to diminish/alter the amount of aggregated and/or congophilic Amylin/IAPP.

In one study, the ability of Amylin/IAPP fibrils to bind Congo red in the absence or presence of increasing amounts of the compounds or DP-68(negative control) (at Amylin/IAPP:test compound weight ratios of 1:1, 1:0.1, 1:0.01 or 1:0.001) was determined. EDTA could just as effectively serve as a negative control. The results of 3-day incubations are presented in Table 2 below. Whereas DP-68 (the negative control) caused no significant inhibition of Amylin/IAPP fibril binding to Congo red at all concentrations tested, the compounds were observed to have a dose-dependent inhibition of Amylin/IAPP binding to Congo red. All of the compounds showed a dose dependent inhibition with compounds 4, 5, and 7-9 displaying the highest amounts of inhibition at an Amylin/IAPP:test compound wt/wt ratio of 1:1 ranging between 54.6% to 88.6%. For example, compound #4 caused a significant ($p<0.01$) 70.8±1.55% inhibition of Congo red binding to Amylin/IAPP fibrils when used at an Amylin/IAPP:test compound wt/wt ratio of 1:1, and a significant ($p<0.01$) 46.0±7.43% inhibition of Congo red binding when used at an Amylin/IAPP:test compound wt/wt ratio of 1:0.1. In another example, compound #7 caused a significant ($p<0.01$) 66.2±7.81% inhibition of Congo red binding to Amylin/IAPP fibrils when used at an Amylin/IAPP:test compound wt/wt ratio of 1:1, and a significant ($p<0.01$) 44.1±5.62% inhibition of Congo red binding when used at an Amylin/IAPP:test compound wt/wt ratio of 1:0.01. This study also indicated that compounds of this invention are potent inhibitors of Amylin/IAPP fibril binding to Congo red, and usually exert their effects in a dose-dependent manner.

TABLE 2

Congo red binding data
% Inhibition Amylin/IAPP (result ± S.D.) at Amylin/IAPP:test compound wt/wt ratio given

| Test Compound # | 1:1 | 1:0.1 | 1:0.01 | 1:0.001 |
|---|---|---|---|---|
| (control) | 0.0 ± 3.47 | 8.7 ± 2.26 | 0.0 ± 9.34 | 0.0 ± 6.29 |
| 1 | 58.1 ± 6.67 | 35.7 ± 5.12 | 7.8 ± 6.13 | 0.0 ± 6.44 |
| 2 | 45.8 ± 1.62 | 33.5 ± 6.38 | 5.2 ± 0.23 | 5.3 ± 6.75 |
| 3 | 60.1 ± 3.78 | 26.0 ± 5.79 | 3.6 ± 1.16 | 7.1 ± 4.14 |
| 4 | 70.8 ± 1.55 | 46.0 ± 7.43 | 8.0 ± 4.62 | 0.0 ± 7.35 |
| 5 | 54.6 ± 14.22 | 43.4 ± 3.39 | 8.3 ± 6.91 | 3.5 ± 2.40 |
| 6 | 80.7 ± 0.75 | 36.4 ± 12.77 | 1.0 ± 4.82 | 5.2 ± 2.31 |
| 7 | 66.2 ± 7.81 | 44.1 ± 5.62 | 14.0 ± 10.73 | 9.1 ± 1.29 |
| 8 | 74.9 ± 1.26 | 39.7 ± 7.20 | 20.2 ± 7.11 | 1.7 ± 1.98 |
| 9 | 88.6 ± 2.08 | 41.2 ± 5.64 | 12.0 ± 8.03 | 16.5 ± 9.88 |

Example 7

Compositions of Compounds of this Invention

The compounds of this invention, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa.

Representative compositions are as follows:

Oral Tablet Formulation

An oral tablet formulation of a compound of this invention is prepared as follows:

|  | % w/w |
| --- | --- |
| Compound of this invention | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates are dried. The dried granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

|  | % w/w |
| --- | --- |
| Compound of this invention | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral formulation

A parenteral formulation is prepared as follows:

|  | % w/w |
| --- | --- |
| Compound of this invention | 1.0 |
| Normal saline | 99.0 |

The compound is dissolved in the saline, and the resulting solution is sterilized and filled into vials, ampoules, and prefilled syringes, as appropriate.

Controlled-Release Oral Formulation

A sustained release formulation may be prepared by the method of U.S. Pat. No. 4,710,384, as follows:

One Kg of a compound of this invention is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

The present invention is not limited in scope by the specific embodiments described herein. Indeed, various modifications of the invention in addition to those described will become apparent to those skilled in the art from the foregoing descriptions. Such modifications are intended to fall within the scope of the appended claims. Various publications are cited herein, the disclosures of which are incorporated by reference in their entireties.

We claim:

1. A method of treating the formation, deposition, accumulation, or persistence of IAPP amyloid or amylin/IAPP fibrils, comprising treating the fibrils with an effective amount of 2,4 bis (3,4 dihydroxyphenyl) imidazole.

2. A method of treating type II diabetes in a mammal suffering therefrom, comprising administration to the mammal of a therapeutically effective amount of 2,4 bis (3,4dihydroxyphenyl) imidazole.

* * * * *